United States Patent [19]

Nakahata et al.

[11] Patent Number: 5,343,150
[45] Date of Patent: Aug. 30, 1994

[54] APPARATUS AND METHOD FOR MEASURING A PHYSICAL PROPERTY OF A SAMPLE USING AN ELECTRON SPIN RESONANCE SPECTRUM OF THE SAMPLE

[75] Inventors: Seiji Nakahata; Kouichi Sogabe; Akira Yamakawa, all of Hyogo, Japan

[73] Assignee: Sumitomo Electric Industries, Ltd., Osaka, Japan

[21] Appl. No.: 98,116

[22] Filed: Jul. 26, 1993

[30] Foreign Application Priority Data

Aug. 6, 1992 [JP] Japan .................. 4-209988

[51] Int. Cl.$^5$ .................. G01V 3/00; G01R 33/20; G01N 24/10; G01N 25/18

[52] U.S. Cl. .................. 324/316; 324/633; 324/642; 324/317; 374/44

[58] Field of Search .................. 374/44; 324/316, 317, 324/633, 642

[56] References Cited

U.S. PATENT DOCUMENTS

| 3,197,692 | 7/1965 | Hyde | 324/317 |
|---|---|---|---|
| 3,304,492 | 2/1967 | Glarum | 324/316 |
| 3,348,135 | 10/1967 | Howgate | 324/316 |
| 3,348,136 | 10/1967 | Nelson et al. | 324/317 |
| 3,350,633 | 10/1967 | Hyde | 324/316 |
| 3,371,271 | 2/1968 | Takeuchi et al. | 324/317 |
| 3,372,331 | 3/1968 | Larson | 324/317 |
| 4,185,237 | 1/1980 | Uehara et al. | 324/317 |
| 4,232,543 | 11/1980 | Eguchi et al. | 374/44 |
| 4,593,248 | 6/1986 | Hyde et al. | 324/317 |
| 4,803,624 | 2/1989 | Pilbrow et al. | 324/316 |
| 5,233,303 | 8/1993 | Bales et al. | 324/316 |

FOREIGN PATENT DOCUMENTS

| 274281 | 12/1989 | German Democratic Rep. . | |
|---|---|---|---|
| 53-133081 | 11/1978 | Japan . | |
| 0175943 | 10/1982 | Japan | 324/316 |
| 0082982 | 5/1985 | Japan | 324/316 |
| 0082983 | 5/1985 | Japan | 324/316 |
| 0155950 | 8/1985 | Japan | 374/44 |
| 0195355 | 8/1989 | Japan | 324/316 |
| 403053149 | 3/1991 | Japan | 374/44 |
| 1330527 | 8/1987 | U.S.S.R. | 374/44 |
| 1485103 | 6/1989 | U.S.S.R. | 374/44 |
| 84/04398 | 11/1984 | World Int. Prop. O. . | |
| 88/01749 | 3/1988 | World Int. Prop. O. . | |

OTHER PUBLICATIONS

"Oxygen Concentration Measurements Using the ESR Line Modification of PCLI Molecules" by Duret et al., Sensors and Actuators B, pp. 266–269 (Jan. 1992).

"Measurements of Pertinent Concentrations of Oxygen in Vivo" by Swartz et al., Magnetic Resonance in Medicine, Aug. 1991, pp. 333–339.

"NMR Imaging of Gas Imbibed into Porous Ceramic" by Lizak et al., Journal of Magnetic Resonance, 1991, pp. 548–557.

"The Intrinsic Thermal Conductivity of AlN" by Glen A. Slack et al. J. Phys. Chem. Solids, vol. 48, No. 7 pp. 641–647 (1987).

"EPR Study of Oxygen Centers in AlN:O" by G. E. Archangelskii et al. P. N. Lebedev Physical Institute K117–K122 (1981).

Primary Examiner—Diego F. F. Guttierrez
Attorney, Agent, or Firm—W. G. Fasse; W. F. Fasse

[57] ABSTRACT

Disclosed herein is a measuring apparatus and a measuring method which can measure a physical property value such as an oxygen content or thermal conductivity of a sample material such as an aluminum nitride sintered body with high accuracy, over the entire material in a short time. A microwave oscillation source generates microwaves. A sample material to be evaluated, such as an aluminum nitride sintered body, is placed in a cavity resonator, irradiated with microwaves (M), and subjected to a magnetic field (H) applied by electromagnets. An amount of microwaves absorbed by the object is measured by a microwave absorption measuring unit. This amount of microwave absorption is obtained from an electron spin resonance spectrum. The concentration of unpaired electrons in the object is obtained from the measured amount of microwave absorption on the basis of a known relation between an amount of microwave absorption and concentration of unpaired electrons. The concentration of unpaired electrons is converted into a physical property value such as an oxygen content or a thermal conductivity value. Such conversion processing is carried out by a computer.

31 Claims, 8 Drawing Sheets

APPARATUS AND METHOD FOR MEASURING A PHYSICAL PROPERTY OF A SAMPLE USING AN ELECTRON SPIN RESONANCE SPECTRUM OF THE SAMPLE

FIELD OF THE INVENTION

The present invention generally relates to a physical property measuring apparatus and a measuring method therefor, and more specifically, it relates to an apparatus for measuring a physical property value of a ceramic material sample based on an electron spin resonance spectrum of the sample, and a measuring method therefor.

DESCRIPTION OF THE BACKGROUND ART

An aluminum nitride sintered body is suitable for use as a material for an IC package or a semiconductor substrate, due to its characteristics such as high theoretical thermal conductivity, excellent electric insulation, etc.

The thermal conductivity of such an aluminum nitride sintered body is determined by amounts of oxygen, carbon, cations etc. which are solidly dissolved in aluminum nitride crystal grains, as described in "J. Phys. Chem. Solids" Vol. 48, No. 7, 1987, pp. 641–647, for example. Thus, it is extremely important to measure such amounts of dissolved substances for quality assurance of an aluminum nitride sintered body having high thermal conductivity. Further, the thermal conductivity of an aluminum nitride sintered body is remarkably influenced by the oxygen content in aluminum nitride crystal grains forming the aluminum nitride raw material powder. Therefore, it is extremely important to measure the oxygen content in the aluminum nitride powder. However, no method of measuring the oxygen content in aluminum nitride powder or a sintered body thereof has been established heretofore.

For example, measurement of an oxygen content by chemical analysis is merely directed to the total amount of impurities of a tested sample. Such impurities include not only the oxygen contained in aluminum nitride particles of an aluminum nitride powder or a sintered body thereof, but also those impurities adhering to the surface or being contained in a grain boundary phase. By using such a chemical analysis, therefore, it is impossible to selectively measure and evaluate only an impurity which is contained in the aluminum nitride crystal grains, i.e. that impurity which has been noted to remarkably influence thermal conductivity.

There is a method of obtaining an oxygen content value by converting an aluminum nitride lattice constant which is measured by X-ray diffraction. When impurities other than oxygen are solidly dissolved in the aluminum nitride crystal grains, however, the lattice constant is not in one-to-one correspondence with the impurity content such as the oxygen content. Thus, this method is also unsuitable for evaluation of aluminum nitride powder or a sintered body thereof.

Measuring an impurity content such as an oxygen content by a surface analysis method such as Auger electron spectroscopy or secondary ion mass spectroscopy is not suitable for the following reasons. First, it is impossible to measure the impurity content if the aluminum nitride crystals contain the impurity in an amount below the detection sensitivity of the measuring method. Second, when the crystals contain the impurity in an amount exceeding the detection sensitivity, on the other hand, impurities which have adhered to a surface of the sample during preparation thereof are also inevitably measured together with those contained in the crystals. Thus, this method is not suitable because of its lack of accuracy in measurement. Third, the amount of time required for the measurement is excessive when the impurity content is measured over a depth of several nm. Fourth, the surface analysis method is directed only to a local region, and is therefore not applicable to evaluation of the overall product.

As described above, it is impossible to detect and measure an impurity such as oxygen contained in the aluminum nitride crystal grains forming an aluminum nitride powder or a sintered body thereof, in a short time over the entire product using the conventional measuring apparatus and method.

Further, quality assurance evaluation as to the thermal conductivity of an aluminum nitride sintered body inevitably depends on the measurement of thermal conductivity by a laser flash method or the like. When using a method of directly measuring thermal conductivity such as the laser flash method, however, a sample for measurement is restricted in size and shape. For example, it is impossible to directly measure thermal conductivity of a product having a thickness of 0.5 mm and a width of 2 to 3 mm. Thus, it is necessary to independently prepare a measurable sample for measuring its thermal conductivity, thereby assuring quality of the product. This is a factor which increases the manufacturing cost. In order to evaluate the quality of a product having a complicated shape, furthermore, a sample is partially cut out to be subjected to measurement of thermal conductivity, thereby carrying out quality evaluation of the product. Thus, it is impossible to evaluate the quality of the overall or entire product.

OBJECTS OF THE INVENTION

An object of the present invention is to provide a measuring apparatus which can measure a physical property value, such as the oxygen content or the thermal conductivity, of a material such as aluminum nitride powder or a sintered body thereof with high accuracy, over the entire material in a short time.

Another object of the present invention is to provide a measuring method which can measure a physical property value, such as the oxygen content or the thermal conductivity, of a material such as aluminum nitride powder or a sintered body thereof with high accuracy, over the entire material in a short time.

SUMMARY OF THE INVENTION

A physical property measuring apparatus according to an aspect of the present invention is adapted to measure a physical property value of a material to be tested, using an electron spin resonance spectrum of the test material. The apparatus of the invention includes a microwave oscillation source, a radiation guide and a radiation cavity, a microwave measuring device, an analyzer and a data converter. The microwave oscillation source generates microwaves. The radiation guide and radiation cavity irradiates the test material such as a ceramic with the microwaves while applying a magnetic field thereto. The microwave measuring device measures an amount of microwaves absorbed in the test material ceramic. The analyzer determines the concentration of unpaired electrons contained in the test material ceramic from the measured amount of microwave absorption in accordance with a known relation between the amount of microwave absorption and the concentration of unpaired electrons in a given test material. The data converter converts the obtained concentration of unpaired electrons into a physical property value.

In the physical property measuring apparatus according to the present invention, a test material such as a ceramic material is provided in the form of a powder or a sintered body. The ceramic material is aluminum nitride or the like. The physical property value to be measured is an oxygen content, thermal conductivity or the like.

In a physical property measuring method according to another aspect of the present invention, microwaves are so generated that an object material to be tested is irradiated with the microwaves during application of a magnetic field. Then, the amount of microwaves absorbed by the object is measured. Thereafter the concentration of unpaired electrons contained in the object material is obtained from the measured amount of microwave absorption in accordance with a known relation between an amount of microwave absorption and a concentration of unpaired electrons in the prescribed material. The obtained concentration of unpaired electrons is converted to a physical property value.

In the physical property measuring method according to the present invention, an object material to be tested is preferably an aluminum nitride sintered body, and the physical property value to be measured is preferably thermal conductivity.

According to the present invention, the amount of microwaves absorbed by the object material is measured. Based on the known relation between an amount of microwave absorption and a concentration of unpaired electrons in the prescribed material, the concentration of unpaired electrons contained in the object material is obtained from the measured amount of microwave absorption. A physical property value is obtained from the concentration of unpaired electrons. Therefore, it is possible to measure the physical property over the entire material with high accuracy in a nondestructive manner. Further, the physical property can be measured in a short time. When the inventive measuring apparatus is automated and incorporated in a production line, therefore, it is possible to carry out quality assurance as to physical properties of all products. Particularly when the physical property measuring apparatus and the measuring method according to the present invention is used for quality evaluation of an aluminum nitride sintered body having high thermal conductivity, it is possible to assure that the aluminum nitride sintered body has a high quality over the entire product.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS AND OF THE BEST MODE OF THE INVENTION

The inventors have studied a method of measuring an amount of microwave absorption from an electron spin resonance absorption spectrum, to find a method of measuring thermal conductivity of aluminum nitride powder or a sintered body thereof based on a relation between an amount of microwave absorption and the concentration of unpaired electrons in a tested material and a relation between the concentration of unpaired electrons and a physical property such as an oxygen content or thermal conductivity of a tested material.

Figure 1:
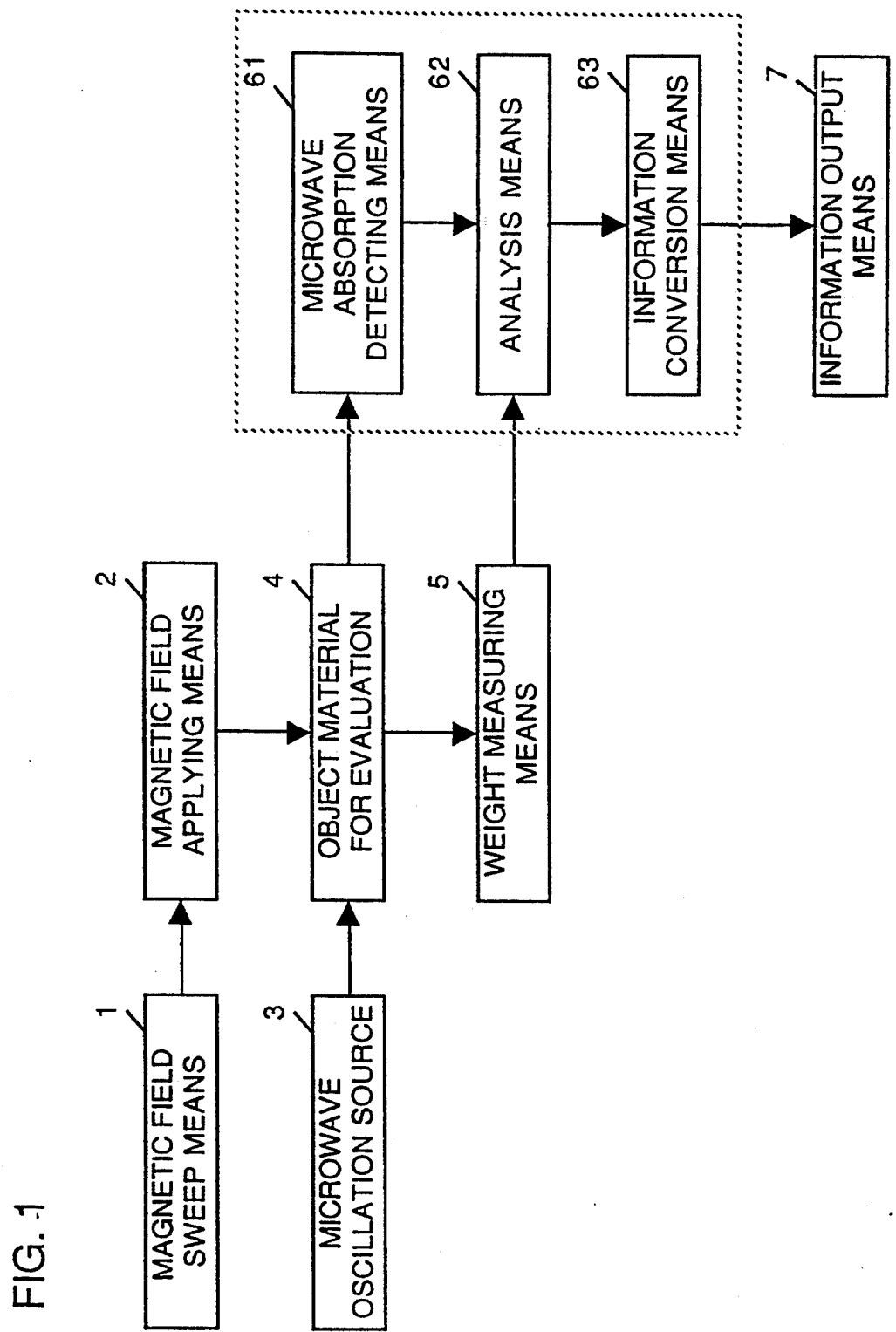
FIG. 1 is a general block diagram functionally illustrating an embodiment of a physical property measuring apparatus according to the present invention.

FIG. 1 is a general block diagram functionally illustrating an embodiment of a physical property measuring apparatus according to the present invention. Referring to FIG. 1, magnetic field sweep controller 1 changes values of currents which are applied to electromagnets forming a magnetic field generator 2. Thus, a magnetic field which is applied to an object material 4 for evaluation is increased or decreased. The object material 4 is irradiated with microwaves which are generated by a microwave oscillation source 3. The object material 4 is thus irradiated with the microwaves, while also being subjected to an increased or decreased magnetic field. Microwave absorption detector 61 measures an amount of microwaves absorbed by the object material 4. Weighing scale 5 measures the weight of the object material 4. Then, an amount of microwave absorption per unit weight is calculated. For example, the concentration of unpaired electrons contained in an aluminum nitride object material is obtained from the measured amount of microwave absorption per unit weight based on a known relation between microwave absorption and concentration of unpaired electrons in aluminum nitride. Analyzer 62 is adapted to carry out the necessary processing for calculating or obtaining the concentration of unpaired electrons. The obtained concentration of unpaired electrons is then converted to a physical property of the aluminum nitride material such as an oxygen content value or thermal conductivity value, for example. Information converter 63 carries out such conversion processing. The obtained physical property value is displayed by information output 7 such as a printer.

Figure 2:
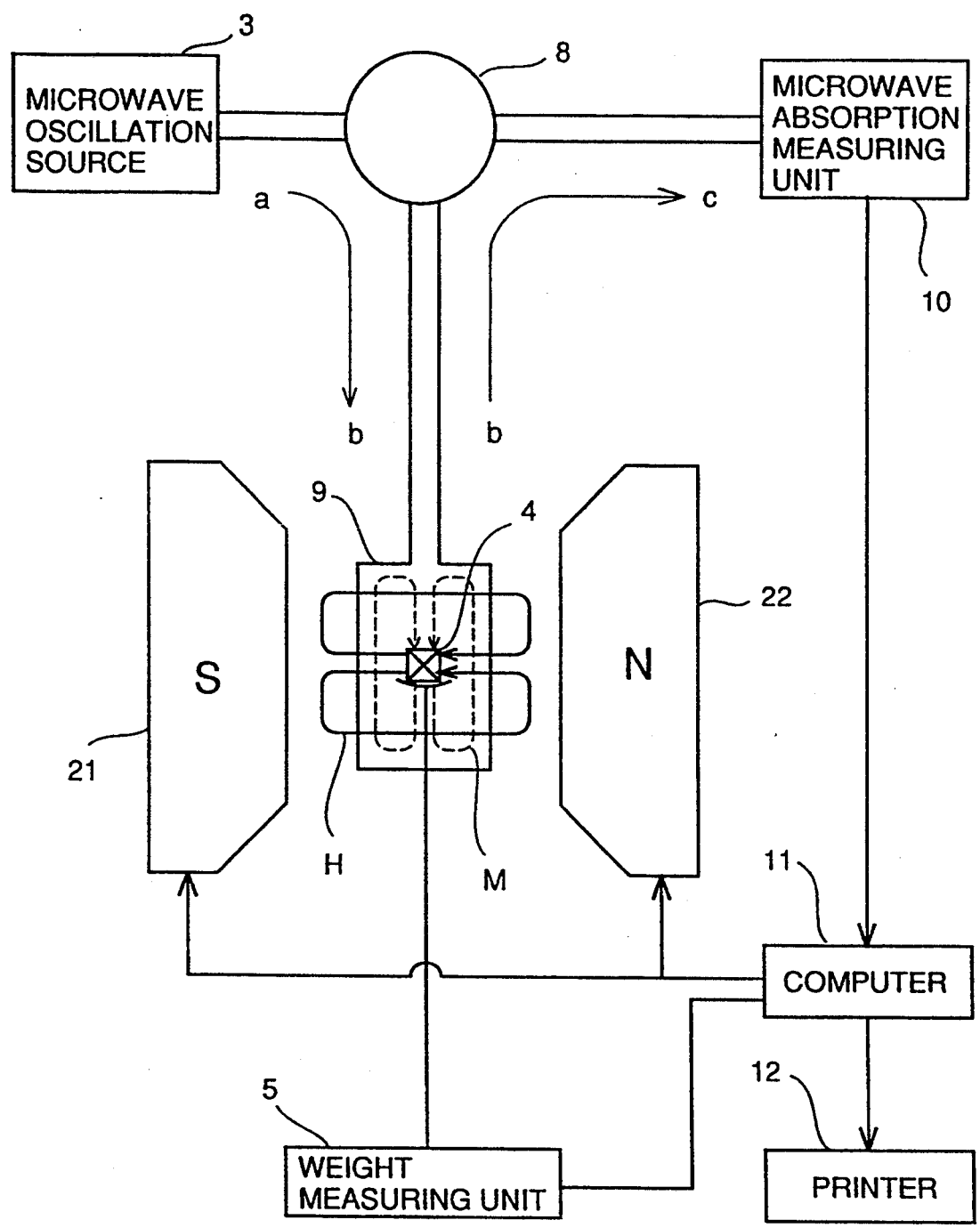
FIG. 2 is a schematic configuration block diagram showing an exemplary configuration of the physical property measuring apparatus according to the present invention.

FIG. 2 is a schematic configuration diagram showing an exemplary configuration of the physical property measuring apparatus based on the general block diagram shown in FIG. 1.

Referring to FIG. 2, microwaves generated by the microwave oscillation source 3 are propagated from "a" to "b" through a circulator 8. Thus, the microwaves are guided to a cavity resonator 9. The object material 4 to be evaluated, such as an aluminum nitride sintered body, is positioned in the cavity resonator 9. Microwaves which are reflected in the cavity resonator 9 are propagated from "b" to "c". A microwave absorption measuring unit 10 measures the reflected propagated microwaves, thereby effectively measuring the amount of microwaves absorbed by the object material 4. In the cavity resonator 9, the object material 4 is irradiated with the microwaves, which are controlled in a direction M perpendicular to a magnetic field H being formed by electromagnets 21 and 22. The magnetic field H is increased or decreased by changes in values of the currents which are applied to the electromagnets 21 and 22. Thus, the object material 4 is irradiated with the microwaves M, while the magnetic field H is varied. A computer 11 changes the values of the currents which are fed to the electromagnets 21 and 22, thereby changing the magnetic field H.

The measured amount of microwave absorption is transmitted to the computer 11. Further, the weight of the object material 4 is measured by a weight measuring unit 5, and transmitted to the computer 11. Thus, the computer 11 calculates an amount of microwave absorption per unit weight. The computer 11 reads and integrates an electron spin resonance absorption spectrum (ESR spectrum) to determine the amount of microwave absorption and then converts the amount of microwave absorption per unit weight to a concentration of unpaired electrons, and further converts the concentration of unpaired electrons to a physical property value such as oxygen concentration or thermal conductivity. A printer 12 displays the physical property value as obtained.

Figure 3:
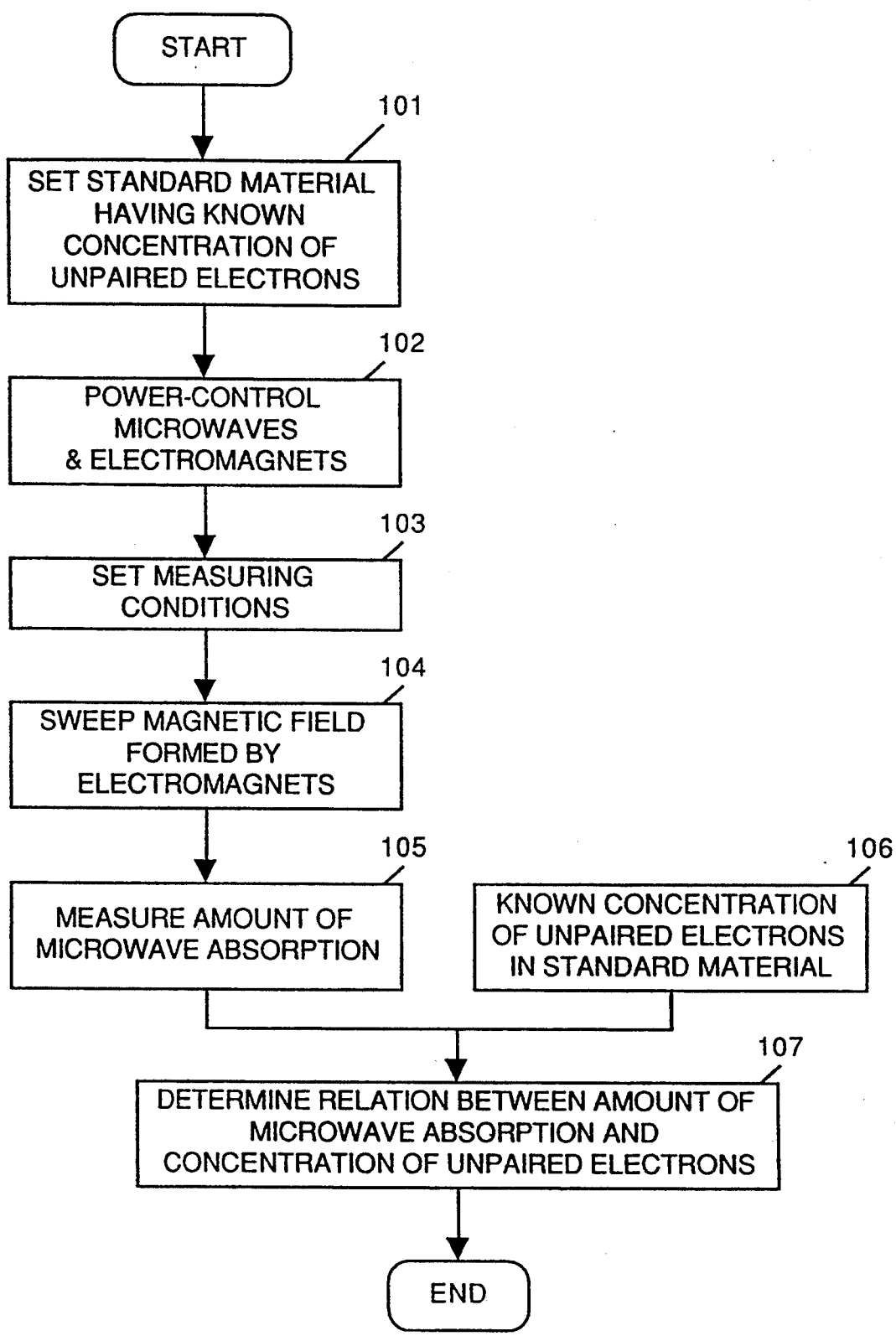
FIG. 3 is a flow chart showing the processing used for obtaining a relation between an amount of microwave absorption and a concentration of unpaired electrons in a measuring method according to the present invention.
Figure 4:
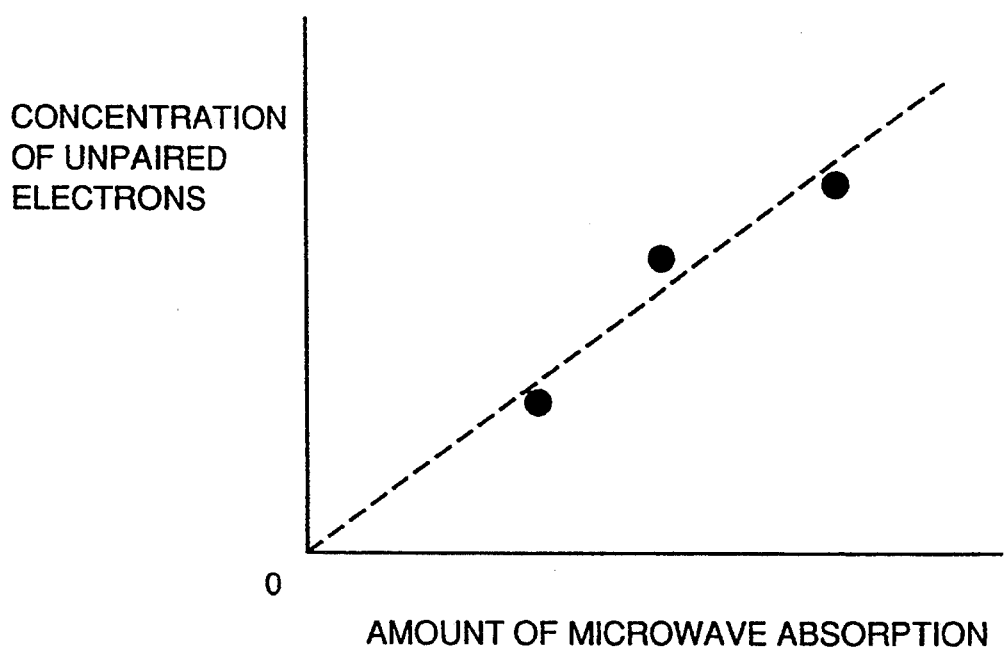
FIG. 4 is a graph illustrating an exemplary relation between an amount of microwave absorption and a concentration of unpaired electrons.

The following is a description of the processing, such as the conversion from the amount of microwave absorption to concentration of unpaired electrons and then from the concentration of unpaired electrons to oxygen concentration or thermal conductivity, which is carried out by the computer 11 of the inventive physical property measuring apparatus shown in FIG. 2, with reference to flow charts and relational expressions. FIG. 3 is a flow chart showing the processing required for obtaining a relation between an amount of microwave absorption and a concentration of unpaired electrons in a tested material such as an aluminum nitride sintered body. Referring to a step 101, a standard material, whose concentration of unpaired electrons is already known, is set in the cavity resonator 9 shown in FIG. 2. Thereafter microwaves and the electromagnets are power-controlled at a step 102. Measuring conditions for the amount of microwave absorption are set at a step 103. A magnetic field generated by the electromagnets is swept at a step 104, and an amount of microwaves absorbed by the standard material is measured at a step 105. The measured amount of microwave absorption is converted to an amount per unit weight of the standard material. A relation between the already known concentration of unpaired electrons in the standard material (step 106) and the amount of microwave absorption per unit weight is determined at a step 107. This relation is obtained by measuring amounts of microwave absorption for several standard materials having known concentrations of unpaired electrons. For example, FIG. 4 shows a relation between an amount of microwave absorption and concentration of unpaired electrons.

Figure 5:
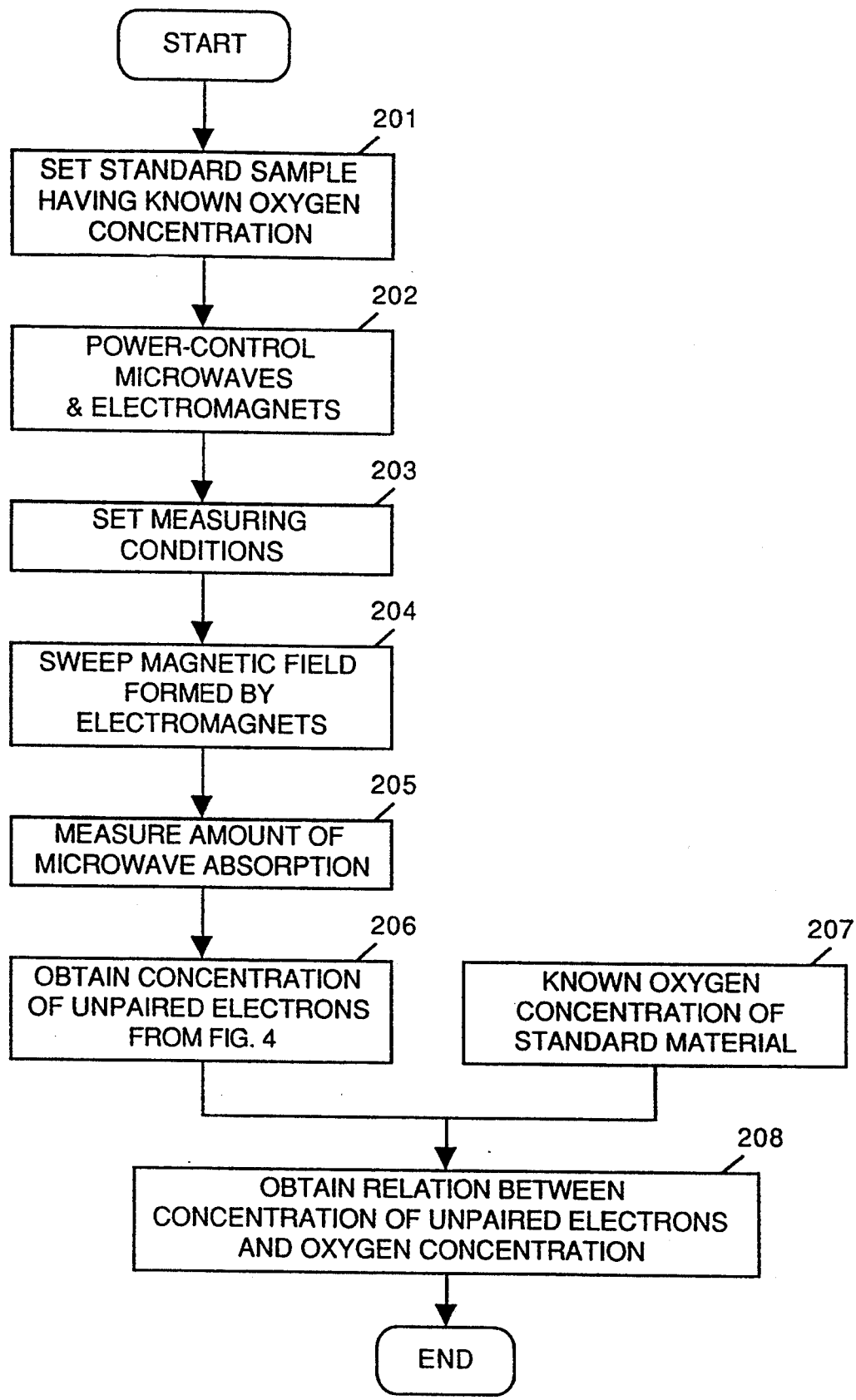
FIG. 5 is a flow chart showing the processing used for obtaining a relation between a concentration of unpaired electrons and an oxygen concentration in the inventive measuring method.
Figure 6:
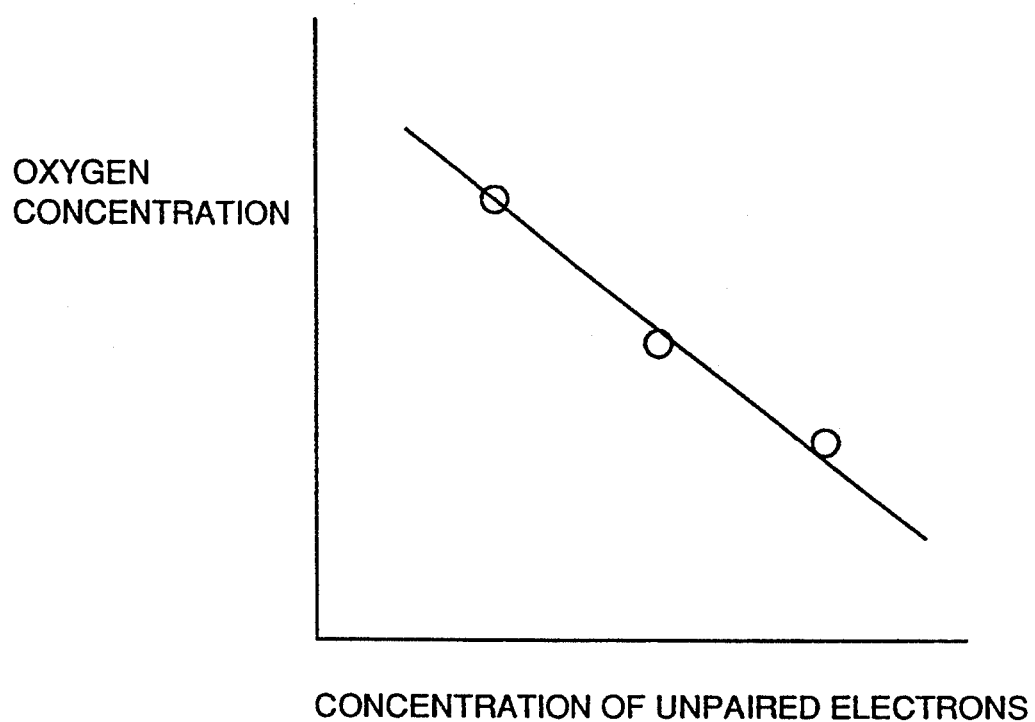
FIG. 6 is a graph showing an exemplary relation between a concentration of unpaired electrons and an oxygen concentration.

FIG. 5 is a flow chart showing the processing required for obtaining a relation between a concentration of unpaired electrons and an oxygen concentration in a prescribed material. First, a standard sample having known oxygen concentration is set in the cavity resonator 9 of the measuring apparatus shown in FIG. 2 at a step 201. Microwaves and the electromagnets are power-controlled at a step 202. Measuring conditions for an amount of microwave absorption are set at a step 203. A magnetic field generated by the electromagnets is swept at a step 204, and an amount of microwaves absorbed by the standard sample is measured at a step 205. At a step 206, the concentration of unpaired electrons is obtained from the amount of microwave absorption on the basis of the relation shown in FIG. 4. The obtained concentration of unpaired electrons is plotted against the known oxygen concentration of the standard material (step 207) so that a relation between the concentration of unpaired electrons and the oxygen concentration is obtained at a step 208. For example, FIG. 6 shows such a relation between the concentration of unpaired electrons and the oxygen concentration.

A relational expression between an oxygen content and a concentration of unpaired electrons in aluminum nitride crystal grains, which has been discovered by the inventors, is now described. Brief description is made regarding the use of standard samples for measurement of oxygen contents or thermal conductivity employed by the inventors for the discovery of this relational expression. These standard samples were prepared from aluminum nitride sintered bodies which were sintered for 100 to 200 hours. Such aluminum nitride sintered bodies were observed with a scanning electron microscope (SEM) and XRD, to confirm that the aluminum nitride sintered bodies serving as standard samples consisted only of aluminum nitride crystal grains having no grain boundary phases. Then, the oxygen contents of the sintered body samples were measured by chemical analysis. Further, values of the concentrations of unpaired electrons of the sintered body standard samples were obtained by the processing shown in FIGS. 3 and 4. From the results of such measurement, the inventors have found that the oxygen content and the concentration of unpaired electrons in aluminum nitride crystal grains are related as follows:

$$\text{oxygen content (wt. \%)} = K/(\text{concentration of unpaired electrons})^n \quad \text{(A)}$$

where K represents a constant, and n represents a value in a range of $1 < n < 2$, which is varied with measuring conditions.

On the other hand, a relation between the thermal conductivity $\lambda$ and the oxygen content in an aluminum nitride sintered body is expressed as follows, as described in "J. Phys. Chem. Solids" Vol 48, No. 7, 1987, pp. 641–647, for example:

$$1/\lambda = 1/\lambda_{pp} + \Delta W \quad \text{(B)}$$

where $\lambda_{pp} = 319$ (W/mK)

$\Delta W/\epsilon = 0.43$ (mK/W)

$\epsilon = \Delta n/n_0$ ($\Delta n$: oxygen concentration, $n_0$: nitrogen concentration)

The expressions (A) and (B) provide:

$1/\lambda = 1/\lambda_{pp} + \{0.11 \ K/(\text{concentration of unpaired electrons})^n\}$ Hence, thermal conductivity $\lambda$ can be obtained from the concentration of unpaired electrons.

Figure 7:
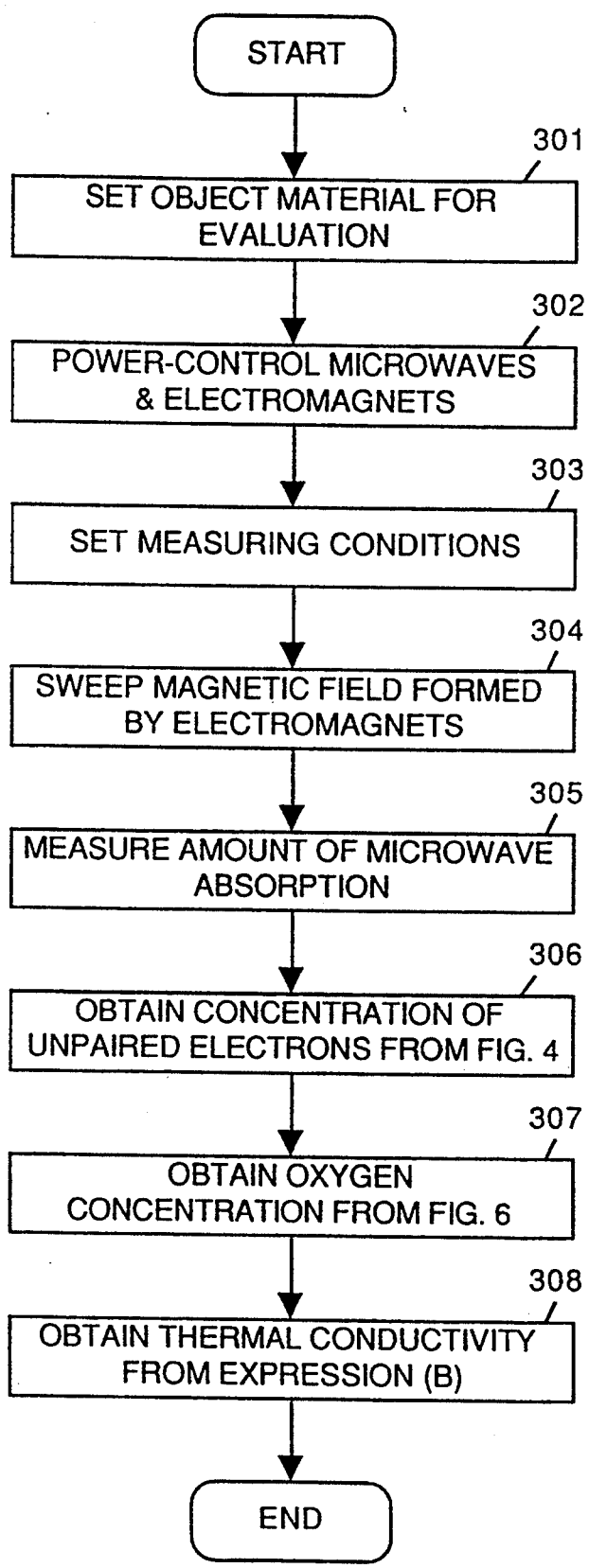
FIG. 7 is a flow chart showing the processing used for obtaining oxygen concentration and thermal conductivity as physical property values from the measurement of an amount of microwave absorption using an unknown object material to be evaluated.

The following is a description of the processing required for determining the thermal conductivity of an aluminum nitride sintered body, which is an unknown object material to be evaluated, using the relation between the amount of microwave absorption and the concentration of unpaired electrons (FIG. 4), the relation between the concentration of unpaired electrons and the oxygen concentration (FIG. 6) and the relation between the oxygen concentration and the thermal conductivity (expression (B)). FIG. 7 is a flow chart showing the processing for obtaining the thermal conductivity by measuring the amount of microwave absorption in the unknown object material to be evaluated.

First, an aluminum nitride sintered body serving as an object material to be evaluated is set in the cavity resonator 9 of the measuring apparatus shown in FIG. 2 at a step 301. Microwaves and the electromagnets are power-controlled at a step 302. Measuring conditions for the amount of microwave absorption are set at a step 303. A magnetic field generated by the electromagnets is swept at a step 304, so that an amount of microwaves absorbed by the object material is measured at a step 305. At a step 306, the concentration of unpaired electrons is obtained from the amount of microwave absorption per unit weight on the basis of the relation shown in FIG. 4. At a step 307, the oxygen concentration is obtained from the concentration of unpaired electrons on the basis of the relation shown in FIG. 6. At a step 308, the thermal conductivity is obtained from the oxygen concentration using the relational expression (B).

Thus, it is possible to obtain oxygen concentration or thermal conductivity values from the amount of microwaves absorbed by an evaluated object material. For example, it is possible to determine the oxygen content and thermal conductivity by measuring the amount of microwaves absorbed by aluminum nitride powder or a sintered body thereof.

Further, it is possible to obtain a relation between oxygen concentration and an amount of microwave absorption or a relation between thermal conductivity and the amount of microwave absorption by measuring the amount of microwaves absorbed by a material having a known oxygen concentration or thermal conductivity, thereby allowing determination of the oxygen content or thermal conductivity of the object material to be evaluated from the amount of microwaves absorbed by the object material to be evaluated.

An electron spin resonance spectrum which is obtained from a sintered body is not influenced by the type of an additive which is generally employed for facilitating a sintering process.

Figure 8:
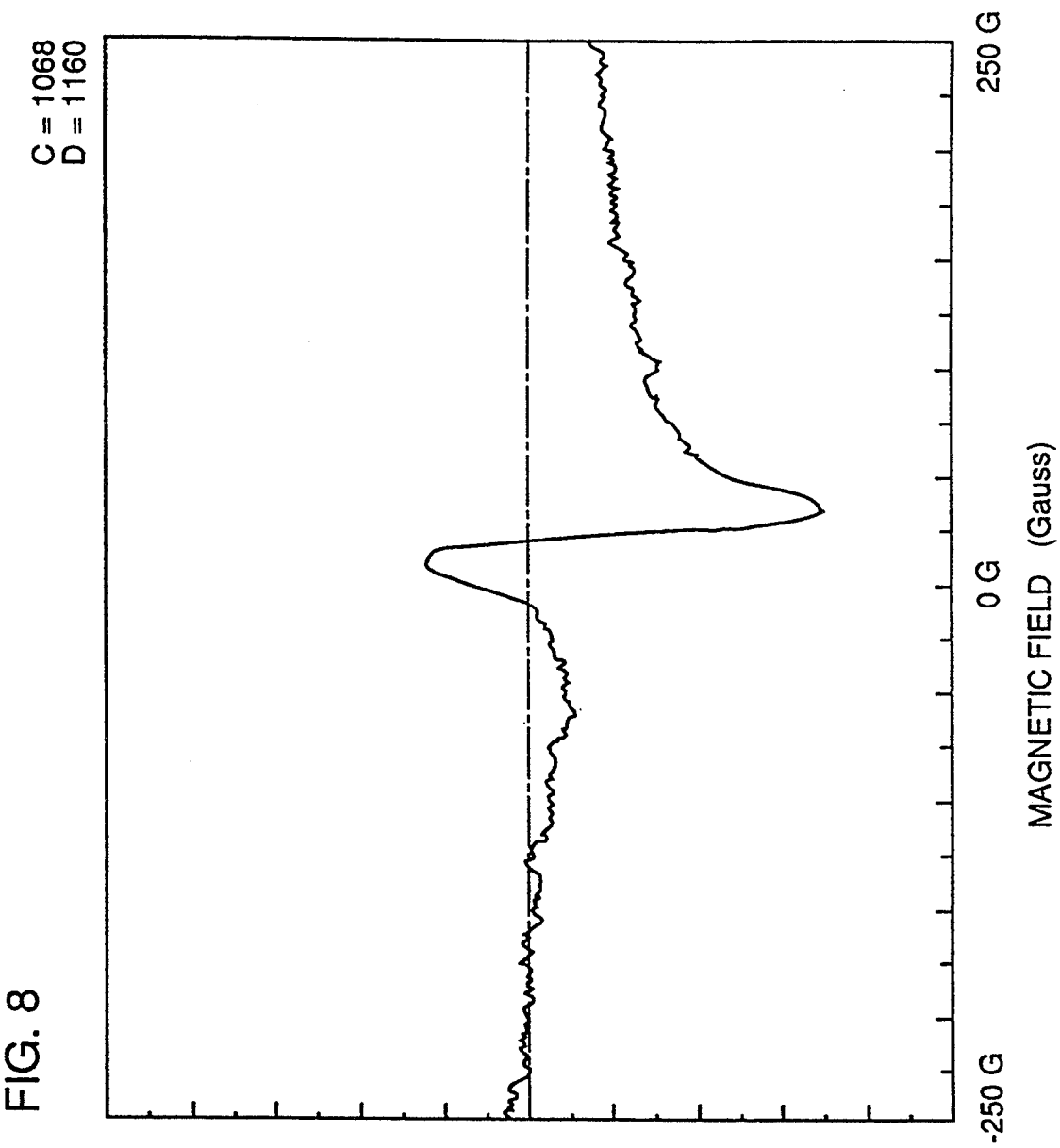
FIG. 8 is a graph showing an electron spin resonance absorption spectrum obtained by irradiating an aluminum nitride sintered body with microwaves.

FIG. 8 illustrates an exemplary electron spin resonance spectrum which is obtained by irradiating an aluminum nitride sintered body with microwaves. Thus, it is possible to obtain a differential curve of the amount of microwave absorption which varies with an increased or decreased magnetic field. Thus, the amount of microwave absorption can be measured by integrating this curve.

The following is a description of examples of measuring oxygen contents and thermal conductivity values of aluminum nitride sintered bodies using the inventive measuring apparatus.

EXAMPLE 1

Powder which was prepared by adding 0.6 percent by weight of $Y_2O_3$, serving as a sintering assistant, and 3 percent by weight in total of PVB serving as a binder and DPB serving as a plasticizer to 100 g of aluminum nitride powder having an impurity oxygen content of not more than 1.0 percent by weight and a mean particle diameter of 1.4 μm was mixed in a ball mill for about 10 hours.

Thereafter, the mixture was dried and granulated, and the obtained powder was molded under a pressure of at least 1.5 t/cm², and debindered at a temperature of 600° C. for 3 hours. The compact thus treated was sintered at atmospheric pressure at a temperature of 1700° C. for 3 hours, in a nitrogen atmosphere.

The aforementioned measuring apparatus was employed to determine an amount of microwave absorption from an electron spin resonance absorption spectrum of the aluminum nitride sintered body, thereby measuring the oxygen content and thermal conductivity. Table 1 shows the results of the measurement. Table 1 also shows the thermal conductivity measured at a temperature of 26° C. by a laser flash method, for the purpose of reference.

EXAMPLES 2 TO 19

Sintering aids shown in Table 1 were added to aluminum nitride powder materials having impurity oxygen contents of not more than 1.0 percent by weight and mean particle diameters of 1.0 to 3.0 μm, which in turn were mixed and molded similarly to Example 1. The obtained compacts were heat treated under conditions shown in Table 1, and 18 types of aluminum nitride sintered bodies were prepared in a similar manner to Example 1.

Table 1 also shows oxygen contents and thermal conductivity values obtained by measuring amounts of microwave absorption which were obtained from electron spin resonance spectra measured using the aforementioned measuring apparatus for each of the obtained aluminum nitride sintered bodies. Table 1 further shows thermal conductivity values measured by a laser flash method, for the purpose of reference.

TABLE 1

|  | Sintering Aid (wt. %) | Sintering Temperature (K) | Sintering Time (hr) | Oxygen Content (wt %) | Thermal Conductivity (1) (W/m · K) | Thermal Conductivity (2) (W/m · K) |
| --- | --- | --- | --- | --- | --- | --- |
| Example 1 | $Y_2O_3$:0.6 | 1700 | 3 | 0.19 | 191 | 199 |

TABLE 1-continued

|  | Sintering Aid (wt. %) | Sintering Temperature (K) | Sintering Time (hr) | Oxygen Content (wt %) | Thermal Conductivity (1) (W/m·K) | Thermal Conductivity (2) (W/m·K) |
|---|---|---|---|---|---|---|
| Example 2 | $YF_3$:0.6 | 1700 | 2 | 0.12 | 224 | 219 |
| Example 3 | YN:0.6 | 1750 | 3 | 0.10 | 236 | 222 |
| Example 4 | $Yb_2O_3$:0.6 | 1800 | 3 | 0.15 | 208 | 235 |
| Example 5 | $TiO_2$:0.6 | 1850 | 5 | 0.41 | 120 | 123 |
| Example 6 | CaO:0.26,$WO_3$:0.6 | 1700 | 3 | 0.28 | 160 | 174 |
| Example 7 | $CaF_2$:0.5 | 1750 | 3 | 0.30 | 154 | 168 |
| Example 8 | $Ca_3N_2$:0.5 | 1750 | 4 | 0.16 | 204 | 182 |
| Example 9 | CaO:1.0 | 1750 | 5 | 0.14 | 214 | 198 |
| Example 10 | BaO:1.0 | 1750 | 5 | 0.23 | 176 | 178 |
| Example 11 | $Nd_2O_3$:1.5 | 1800 | 5 | 0.19 | 191 | 215 |
| Example 12 | $Sm_2O_3$:1.5 | 1800 | 5 | 0.14 | 214 | 204 |
| Example 13 | $Gd_2O_3$:1.5 | 1800 | 5 | 0.10 | 236 | 223 |
| Example 14 | $Dy_2O_3$:1.5 | 1800 | 5 | 0.09 | 242 | 239 |
| Example 15 | $Tm_2O_3$:1.5 | 1800 | 5 | 0.14 | 214 | 204 |
| Example 16 | $La_2O_3$:1.5 | 1800 | 5 | 0.16 | 204 | 220 |
| Example 17 | $HfO_2$:1.5 | 1800 | 5 | 0.31 | 152 | 155 |
| Example 18 | $Y_2O_3$:1.5, $CaF_2$:0.5 | 1850 | 10 | 0.07 | 256 | 249 |
| Example 19 | $Y_2O_3$:1.5, $Ca_3N_4$:0.5 | 1850 | 12 | 0.05 | 271 | 258 |

Thermal Conductivity (1): obtained according to inventive apparatus and method
Thermal Conductivity (2): measured according to laser flash method According to the present invention, as hereinabove described, it is possible to measure a physical property value such as an oxygen content or thermal conductivity of a material to be tested, such as an aluminum nitride powder or a sintered body thereof, with high accuracy over the entire material, in a short period of time and in a nondestructive manner. When the inventive measuring apparatus and method are automated and incorporated in a production line, therefore, it is possible to carry out quality assurance testing as to physical property values of all products.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An apparatus for measuring a physical property value of a material to be tested, said apparatus comprising a microwave oscillation source which generates microwaves, a magnetic field generator which applies a magnetic field to the test material, a radiation guide which guides said microwaves to irradiate the test material, a microwave measuring device which measures an amount of microwaves absorbed by the test material, an analyzer which determines a concentration of unpaired electrons in the test material using said measured amount of microwave absorption and using a predetermined standard relation between microwave absorption and concentration of unpaired electrons in standard materials of the same type as the test material, and a data converter which converts said concentration of unpaired electrons into the physical property value to be measured.

2. The apparatus of claim 1, wherein the physical property to be measured is an oxygen content, and wherein said data converter comprises an oxygen content determining data converter which converts said concentration of unpaired electrons into the oxygen content.

3. The apparatus of claim 1, wherein the physical property to be measured is a thermal conductivity and wherein said data converter comprises a thermal conductivity determining data converter which converts said concentration of unpaired electrons into the thermal conductivity.

4. The apparatus of claim 1, wherein the magnetic field generator comprises an electromagnet.

5. The apparatus of claim 1, further comprising a magnetic field controller which controls said magnetic field generator to sweep said magnetic field through a varying field intensity.

6. The apparatus of claim 5, wherein said microwave measuring device comprises a detector, which determines an electron spin resonance spectrum of the test material while said magnetic field controller sweeps the magnetic field, and comprises an integrator which integrates said spectrum to determine said amount of microwaves absorbed by the test material.

7. The apparatus of claim 1, further comprising a weighing scale which weighs the test material and provides weight data for determining said measured amount of microwave absorption as a microwave absorption per unit weight.

8. The apparatus of claim 1, wherein said radiation guide comprises a microwave radiation circulator and a microwave resonance cavity.

9. The apparatus of claim 1, further comprising a computer including an analyzer circuit which forms said analyzer and a data converter circuit which forms said data converter.

10. The apparatus of claim 1, wherein said data converter includes and uses a standard relation between concentration of unpaired electrons and the physical property value to be measured for standard materials of the same type as the test material.

11. A physical property value measuring system comprising the apparatus of claim 1 in combination with the material to be tested.

12. The system of claim 11, wherein said material to be tested comprises a ceramic material.

13. The system of claim 12, wherein said ceramic material comprises a powder ceramic material.

14. The system of claim 13, wherein said powder ceramic material comprises an aluminum nitride powder.

15. The system of claim 12, wherein said ceramic material comprises a ceramic sintered body.

16. The system of claim 15, wherein said ceramic sintered body comprises an aluminum nitride sintered body.

17. A method of measuring a physical property value of a material to be tested, said physical property measuring method comprising the steps of: providing a test material; generating microwaves; generating a magnetic field; applying said magnetic field to the test material; guiding said microwaves to irradiate the test material while applying said magnetic field to said test material; measuring an amount of microwaves absorbed by said test material; determining a concentration of unpaired electrons in the test material by using said measured amount of microwave absorption and using a predetermined standard relation between microwave absorption and concentration of unpaired electrons in standard materials of the same type as the test material; and converting said concentration of unpaired electrons into the physical property value to be measured.

18. The method of claim 17, wherein the physical property value to be measured is a thermal conductivity value and said step of converting comprises converting said concentration of unpaired electrons into said thermal conductivity value.

19. The method of claim 18, wherein the step of providing a test material comprises providing an aluminum nitride sintered body.

20. The method of claim 18, wherein said step of converting said concentration of unpaired electrons into said thermal conductivity value is carried out according to the equation $$1/\lambda = 1/\lambda_{pp} + [0.11 \, K/(\text{concentration of unpaired electrons})]^n$$

where $\lambda$ is the thermal conductivity value, $\lambda_{pp}=319$ (W/mK), K is a constant, and n is in the range $1<n<2$.

21. The method of claim 17, wherein the physical property value to be measured is an oxygen content and said step of converting comprises converting said concentration of unpaired electrons into said oxygen content.

22. The method of claim 21, wherein the step of providing a test material comprises an aluminum nitride powder.

23. The method of claim 21, wherein the step of providing a test material comprises providing an aluminum nitride sintered body.

24. The method of claim 21, wherein said step of converting said concentration of unpaired electrons into said oxygen content is carried out according to the equation:

$$\text{oxygen content (wt. \%)} = K/(\text{concentration of unpaired electrons})^2,$$

where K is a constant and n is in the range $1<n<2$.

25. The method of claim 17, further comprising a step of sweeping said magnetic field through a varying field intensity.

26. The method of claim 25, wherein said step of measuring an amount of microwaves absorbed comprises a step of determining an electron spin resonance spectrum during said sweeping of said magnetic field.

27. The method of claim 26, wherein said step of measuring an amount of microwaves absorbed further comprises a step of integrating said spectrum.

28. The method of claim 17, further comprising a step of weighing the test material and providing weight data for determining said measured amount of microwave absorption as a microwave absorption per unit weight.

29. The method of claim 17, wherein said step of converting comprises using said determined concentration of unpaired electrons and using a standard relation between concentration of unpaired electrons and the physical property value to be measured for standard material of the same type as the test material.

30. The method of claim 17, wherein the method is automated by providing a computer to carry out the steps of determining a concentration of unpaired electrons and converting said concentration into the physical property value.

31. The method of claim 30, further comprising controlling said step of applying said magnetic field to the test material using said computer.

* * * * *

UNITED STATES PATENT AND TRADEMARK OFFICE
CERTIFICATE OF CORRECTION

PATENT NO.   : 5,343,150
DATED        : August 30, 1994
INVENTOR(S)  : Seiji Nakahata, et al It is certified that error appears in the above-indentified patent and that said Letters Patent is hereby corrected as shown below:

```
Col. 7, line 11, replace "0.11" by --0.011--.
Claim  4, (col. 10, line 27, replace "the" by --said--.
Claim 14, (col. 10, line 66), replace "," by --.--.
Claim 20, (col. 11, line 35), replace "0.11" by --0.011--.
Claim 22, (col. 12, line  2), after "comprises" insert
                              --providing--.
Claim 24, (col. 12, line 13), replace "electrons)²" by
                              --electrons)$^n$--.
Claim 29, (col. 12, line 34), replace "material" (first
                              occurrence) by --materials--.
```

Signed and Sealed this

Eighth Day of November, 1994

Attest:

BRUCE LEHMAN

Attesting Officer        Commissioner of Patents and Trademarks